(12) United States Patent
Saini

(10) Patent No.: US 11,844,729 B2
(45) Date of Patent: Dec. 19, 2023

(54) COMPREHENSIVE INTRAOCULAR VISION ADVANCEMENT

(71) Applicant: Manjinder Saini, Germantown, TN (US)

(72) Inventor: Manjinder Saini, Germantown, TN (US)

( * ) Notice: Subject to any disclaimer, the term of this patent is extended or adjusted under 35 U.S.C. 154(b) by 0 days.

(21) Appl. No.: 18/094,350

(22) Filed: Jan. 7, 2023

(65) Prior Publication Data
US 2023/0149220 A1    May 18, 2023

Related U.S. Application Data

(63) Continuation of application No. 17/716,670, filed on Apr. 8, 2022, now Pat. No. 11,547,608, which is a continuation-in-part of application No. 16/854,766, filed on Apr. 21, 2020, now Pat. No. 11,564,840, and a continuation-in-part of application No. 16/848,650, filed on Apr. 14, 2020, now Pat. No. 11,696,853, which is a continuation of application No. 15/812,294, filed on Nov. 14, 2017, now Pat. No. 10,617,567, and a continuation of application No. 15/812,433, filed on Nov. 14, 2017, now Pat. No. 10,624,791.

(60) Provisional application No. 63/173,019, filed on Apr. 9, 2021, provisional application No. 62/517,894, filed on Jun. 10, 2017.

(51) Int. Cl.
*A61F 2/16* (2006.01)
*A61F 9/08* (2006.01)

(52) U.S. Cl.
CPC .............. *A61F 9/08* (2013.01); *A61F 2/1624* (2013.01); *A61F 2250/0002* (2013.01)

(58) Field of Classification Search
CPC ........ A61F 2/1624; A61F 2/1548; A61F 9/08; A61F 2250/0001; A61F 2250/0002; A61F 2250/0004; A61F 2250/0008; A61F 2250/0091
See application file for complete search history.

(56) References Cited

U.S. PATENT DOCUMENTS 5,653,751 A  *  8/1997  Samiy .................... A61F 9/08
                                              623/6.63
7,001,427 B2 *  2/2006  Aharoni ............... A61F 2/1651
                                              623/4.1

(Continued)

*Primary Examiner* — Paul B Prebilic
(74) *Attorney, Agent, or Firm* — Holland & Knight LLP; Matthew C. Cox

(57) ABSTRACT

An intraocular implant device for comprehensive intraocular vision advancement includes an intraocular implant body shaped for positioning inside a lens chamber of an eye. In some embodiments, the implant includes an optical adjustable base accommodating lens configured to provide both base adjustment and accommodation. In further embodiments, the implant includes a photoelectric sensor operable to receive incident light through the cornea and to convert the received light into electrical energy for use with one or more circuit components disposed on the body, and wherein the photoelectric sensor is also operable to convert the received light into image data. The ocular implant device may include a projector for projecting the an image representative of the image data onto the retina of a user.

7 Claims, 16 Drawing Sheets

(56) References Cited

U.S. PATENT DOCUMENTS

| | | | | |
|---|---|---|---|---|
| 7,041,133 B1 * | 5/2006 | Azar | ................... | A61F 2/1618 |
| | | | | 623/6.22 |
| 8,197,539 B2 * | 6/2012 | Nasiatka | ................... | A61F 9/08 |
| | | | | 607/54 |
| 2013/0194540 A1 * | 8/2013 | Pugh | ................ | B29D 11/00817 |
| | | | | 623/6.11 |
| 2013/0258275 A1 * | 10/2013 | Toner | ................... | A61F 2/1627 |
| | | | | 623/6.22 |
| 2013/0278887 A1 * | 10/2013 | Legerton | ................ | G02C 7/049 |
| | | | | 351/158 |
| 2015/0378176 A1 * | 12/2015 | Flitsch | .................. | A61F 2/1648 |
| | | | | 623/6.56 |
| 2017/0189170 A1 * | 7/2017 | Haddock | ............ | H04B 10/1141 |

* cited by examiner

COMPREHENSIVE INTRAOCULAR VISION ADVANCEMENT

CROSS-REFERENCES TO RELATED APPLICATIONS

This application is a continuation of and claims priority to and benefit of U.S. patent application Ser. No. 17/716,670 filed Apr. 8, 2022 entitled COMPREHENSIVE INTRAOCULAR VISION ADVANCEMENT now issued as U.S. Pat. No. 11,547,608, which is a non-provisional of U.S. Provisional Patent Application No. 63/173,019 filed Apr. 9, 2021 and which is also a continuation-in-part of U.S. patent application Ser. No. 16/854,766 filed Apr. 21, 2020, which is a continuation of U.S. patent application Ser. No. 15/812,433 filed Nov. 14, 2017, which is a non-provisional of U.S. Provisional Patent Application No. 62/517,894, all of which are incorporated by reference in their entireties. This application is a continuation of and claims priority to and benefit of U.S. patent application Ser. No. 17/716,670 filed Apr. 8, 2022 now issued as U.S. Pat. No. 11,547,608, which is a non-provisional of U.S. Provisional Patent Application No. 63/173,019 filed Apr. 9, 2021 and which is also a continuation-in-part of U.S. patent application Ser. No. 16/848,650 filed Apr. 14, 2020, which is a continuation of U.S. patent application Ser. No. 15/812,294 filed Nov. 14, 2017, which is a non-provisional of U.S. Provisional Patent Application No. 62/517,894, all of which are incorporated by reference in their entireties.

STATEMENT REGARDING FEDERALLY SPONSORED RESEARCH OR DEVELOPMENT

Not Applicable.

REFERENCE TO SEQUENCE LISTING OR COMPUTER PROGRAM LISTING APPENDIX

Not Applicable.

BACKGROUND

The present disclosure relates generally to ophthalmologic devices for implantation into the eye, and more particularly to intraocular implant devices and associated power supplies for enhancing or restoring vision in humans and animals.

Over the last few decades, vision related problems in rate of occurrence, age of onset, and severity are becoming increasingly worse to the point it is becoming alarming in the vision care industry. One cause appears to be humans increasingly spending more time viewing electronic display screens. Over time, although display technology improved, people began spending more time looking at electronic displays, including home computers, televisions and mobile electronic devices, often in harsh environments such as full sunlight. As people continue to spend more and more time viewing electronic displays such as small screens in harsh conditions such as sunlight, vision problems continue to increase.

Many people experience impaired vision as a result of corneal dysfunction or damage, lens dysfunction or damage, or other conditions of the eye that lead to inability of light to properly pass through the eye to the retina. Various medical procedures have been developed to attempt to correct these types of problems to improve or to restore vision. For example, lens replacement procedures are often used to remove a damaged or occluded lens from the eye. An artificial intraocular lens implant may be inserted into the eye through a small incision in the cornea during a surgical procedure to replace the removed lens. Such procedures are helpful to improve conditions such as cataracts or occluded lenses.

However, such conventional procedures for replacing occluded or damaged lenses with replacement intraocular lens implants are often inadequate to restore or enhance vision of patients with corneal conditions. As light initially enters the eye through the cornea, any conditions of the cornea which scatter or block light are generally not amenable to treatment via artificial lens replacement procedures. Although many corneal replacement procedures do exist, they are often inadequate in improving or restoring sight. Additionally, such procedures require extensive healing times and may cause other complications in the eye.

What is needed are improvements in devices and methods for improving or restoring vision in patients with impaired cornea or lens tissue in the eye.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The present disclosure provides comprehensive intraocular vision advancement (CIVA) using a variety of different embodiments. In some embodiments, a purely optical vision correction or vision enhancement platform provides an adjustable base accommodating lens (ABAL). The adjustable base accommodating lens (ABAL) includes one or more optical elements disposed in an intraocular implant that operate to optically correct or enhance light passing through the eye toward the retina to achieve an adjustable base configuration. As a user ages or develops vision-related changes in eyesight, such as but not limited to presbyopia, the adjustable base accommodating lens can be selectively configured to provide different base and/or accommodation settings to provide far vision correction and/or accommodation for correcting near vision. In some embodiments, the adjustable base accommodating lens includes a plurality of lenses within the intraocular implant that can be mechanically adjusted in relation to each other and in relation to the eye to achieve adjustable base accommodation. In further embodiments, adjustable base accommodating lens (ABAL) may be adjusted by remote input from a user or physician. In further embodiments the adjustable base accommodating lens (ABAL) may employ one or more variable refractive index lenses within the intraocular implant.

In additional embodiments, digital vision advancement includes a magie digitale ("MAGITAL") solution to provide transmission of digital content to the intraocular lens implant for use within the eye. In further embodiments, the comprehensive intraocular vision advancement device and methods of the disclosure provides a dual optical and digital solution including digital information mixed into an optical vision stream ("MIXITAL"). Alternatively, the present disclosure provides systems including a full digital replacement of the optical vision stream wherein a user's eye becomes a monitor for digital content ("MONITAL").

In further embodiments, the present disclosure provides numerous devices, methods and modes of activating an intraocular implant inside the eye. In some embodiments, a transmitter may be housed inside a user's mouth to transmit control signals and/or data to the intraocular implant. For example, one or more buttons may be placed on a tooth. The button may be activated by a user's tongue or with the touch of a finger. Upon activation of the button a control signal may be transmitted wirelessly to a receiver in the intraocular implant, or a peripheral device with a receiver. In some embodiments, an array of buttons on teeth inside the mouth may be provided to provide wireless input to the intraocular implant or to an external peripheral device. In such embodiments, the button array may be used as a keyboard to provide text communications. The button array may communicate to any suitable external device such as a mobile phone or other external peripheral device with a receiver. In some applications, the basic function of the one or buttons is to communicate with intraocular implant. In some embodiments, a user may activate the implant using an external input, such as tapping a user's teeth together according to a control sequence to activate, de-activate, or change programming modes of the implant. Other external control modalities may include a hardware-based control such as a control on a mobile device or a peripheral device with a transmitter that user may wear, such as a watch or ring. In other embodiments, any suitable peripheral including a transmitter may be used to activate, de-activate or change programming modes of the intraocular implant device.

One aspect of the present disclosure provides an intraocular photoelectric power supply system (IO-PEPS) for providing power to one or more microelectronic devices implanted into a human or animal eye. The intraocular photoelectric power supply system provides an implant shaped and sized to fit inside the intraocular lens chamber after a natural lens has been removed. The implant device of the intraocular photoelectric power supply system may be inserted into the lens chamber through a small hole in the cornea utilizing conventional lens replacement surgical tools and techniques. The implant device includes one or more photo-sensors, such as but not limited to a photoelectric device configured to convert incident light into electricity, such as a photovoltaic cell. The photo-sensor or photo-sensor array is positioned on the anterior side of the implant device such that light passing through the cornea will be incident on the sensor or sensor array when the implant device is housed in the lens chamber of the eye. The incoming light irradiating the sensor or sensor array is converted to electricity, which is then available for use by other electronics included on the implant device or otherwise installed within the eye. The incoming light may be specifically tuned to a desired frequency, wavelength, quantity, etc. for optimized power generation using the photoelectric device. The generated electricity may be used immediately, or may be stored in a power storage medium such as a battery on the implant or in the eye for later use.

Another aspect of the present disclosure includes an intraocular projection device configured for implantation into an intraocular cavity formed in the lens chamber after a natural lens is removed. The projector implant device, or artificial projector lens implant, includes an implant having an anterior side oriented toward the cornea and a posterior side oriented toward the retina. An optical light emitter, or projector, is installed on the implant posterior side of the implant facing back into the eye toward the retina. The projector is operable to emit light from the implant located in the lens chamber through the eye toward the retina, thereby forming a desired light pattern on the retina. The emitted light pattern from the projector corresponds to an image to be processed by the user's brain, and may simulate a natural light array associated with a real or artificial image. The projector implant device is miniaturized such that the projector is compact enough to fit on a normal-sized lens implant in the intraocular lens chamber after removal of the natural lens of the eye.

In some embodiments, the implant includes both a projector and a photoelectric device of an intraocular photoelectric power supply to provide electrical power for the projector. The projector is positioned on the posterior side of the lens implant facing the retina, and the photoelectric array is positioned on the anterior side of the implant facing the cornea. Natural or artificial light entering the cornea is incident on the photoelectric array on the anterior side of the implant inside the lens chamber, and the electrical power generated by the photoelectric array is transferred to the projector located on the posterior side of the implant facing the retina. The generated electrical power is used to power the projector to emit photons in a light pattern corresponding to a desired image onto the retina.

Another aspect of the present disclosure provides an intraocular implant device configured for implantation into the lens chamber after removal of a natural lens. The intraocular lens implant device includes a projector on the posterior side facing toward the retina, a photoelectric array on the anterior side facing toward the cornea, and an external light source spaced from the eye configured to irradiate a beam of light through the cornea onto the photoelectric array. The light from the light source is tuned to provide optimal photoelectric conversion into electricity using the specific photoelectric material installed on the implant. The external light source may be operated with an intensity much higher than natural light because the light from the light source is not incident on the retina, but is rather blocked by the artificial intraocular lens implant and used for photoelectric generation of electric power for use by microelectronics within the eye such as but not limited to the projector on the intraocular implant device.

Yet another aspect of the present disclosure provides an intraocular implant device configured for implantation into the lens chamber after removal of a natural lens, wherein the intraocular lens implant device includes an autofocusing digital camera in addition to the projector and photoelectric array. In this aspect, the projector is positioned on the posterior side of the lens implant facing the retina, and the autofocusing digital camera and photoelectric array are positioned on the anterior side of the implant facing the cornea. Natural or artificial light entering the cornea is incident on the photoelectric array on the anterior side of the implant inside the lens chamber, and the electrical power generated by the photoelectric array is transferred to both the autofocusing digital camera located on the anterior side of the implant and the projector located on the posterior side of the implant facing the retina. The generated electrical power is used to power the autofocusing digital camera to receive incident light through the cornea, actively adjust the lens to focus the incident light, convert the focused incident light into focused image data, and send focused image data to the projector. Additionally, the generated electrical power is also used to power the projector to emit photons in a light pattern corresponding to the focused image data onto the retina.

A refraction adjustment unit is provided in yet another aspect of the present disclosure. The refraction adjustment unit provides an intraocular implant device configured for implantation into the lens chamber after removal of a natural lens. The intraocular lens implant device includes an autofocusing electromechanical lens array, a photoelectric array, and a controller, wherein both the autofocusing electromechanical lens array and the photoelectric array are positioned on the anterior side of the implant facing the cornea and the controller is positioned to be in communication with the autofocusing electromechanical lens array. Natural or artificial light entering the cornea is incident on both the autofocusing electromechanical lens array and the photoelectric array on the anterior side of the implant inside the lens chamber, and the electrical power generated by the photoelectric array is transferred to the controller and autofocusing electromechanical lens array. The generated electrical power is used to power the controller to analyze the incoming light incident on the autofocusing electromechanical lens array as it passes through the lens array and to actively adjust the autofocusing electromechanical lens array until the incident light is focused, whereby the focused incident light passes through the autofocusing lens array and to the retina.

Other aspects of the present disclosure also provide for a glucose sensor or intraocular pressure sensor to be used in combination with any of the disclosed elements of an intraocular lens implant. The glucose sensor can be operable to measure certain glucose data from a user's intraocular eye fluids, and wirelessly send the glucose data for an external receiver to receive, analyze, and store. Similarly, the intraocular pressure sensor can be operable to measure pressure levels in a user's lens cavity, and wirelessly send the intraocular pressure data for an external receiver to receive, analyze, and store.

A further objective of the present disclosure is to provide a magie digitale, or "magital" solution to vision advancement. In some embodiments, the devices and methods disclosed herein may be controlled by a user's voice commands to change accommodation setting or to change other settings such as focus, autofocus, on/off state, image capture, data transmission or other features.

Numerous other objects, advantages and features of the present disclosure will be readily apparent to those of skill in the art upon a review of the following drawings and description of a preferred embodiment.

DETAILED DESCRIPTION

Figure 1:
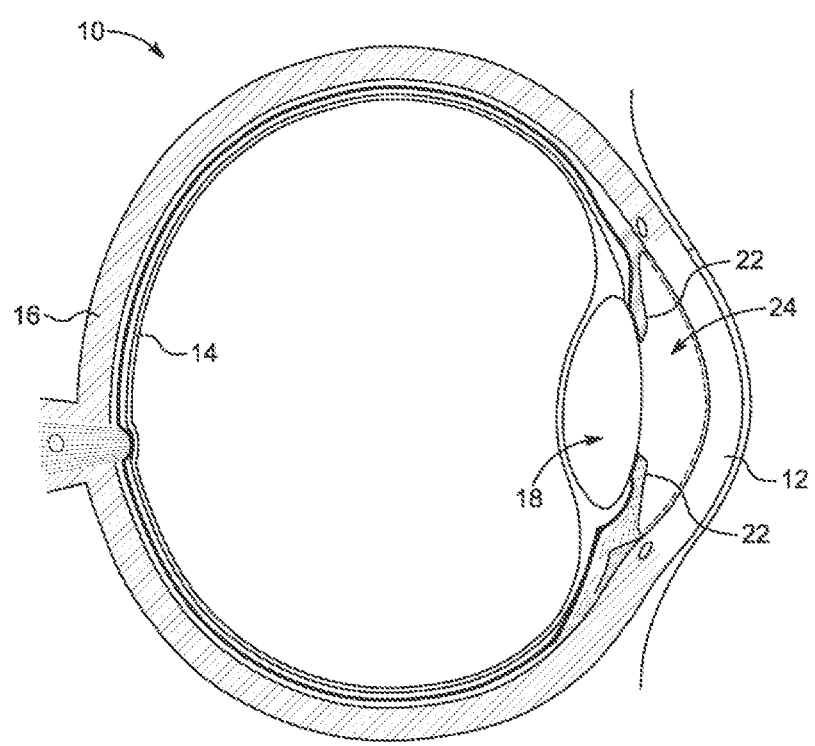
FIG. 1 is a schematic view of an embodiment of an eye with an open lens chamber having a natural lens removed.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing, or as otherwise described. A person of skill in the art will recognize that the apparatus can assume different orientations when in use.

Referring now to the drawings, FIG. 1 illustrates an example schematic of an eye 10, showing a cornea 12 through which light initially enters the eye. Eye 10 includes a retina 14 on the opposite side of the eye positioned to receive the incoming light. The sclera 16 surrounds the exterior of the eye 10. A lens is typically positioned in lens chamber 18. The iris 22 provides an opening allowing light to pass from the anterior chamber 24 into the lens chamber 18. Many conventional procedures are currently known for removal of a damaged or occluded lens from lens chamber 18. For example, in cataract surgery a damaged lens may be phaco-emulsified using a tool to break up the lens. The broken-up lens may then be aspirated from the eye using a negative pressure, and replaced with a liquid solution to maintain the form of the empty lens chamber 18. Following such procedures, an artificial intraocular lens implant is inserted into the empty lens chamber 18 using known tools and techniques. Such implant procedures are easily reversed.

Figure 2:
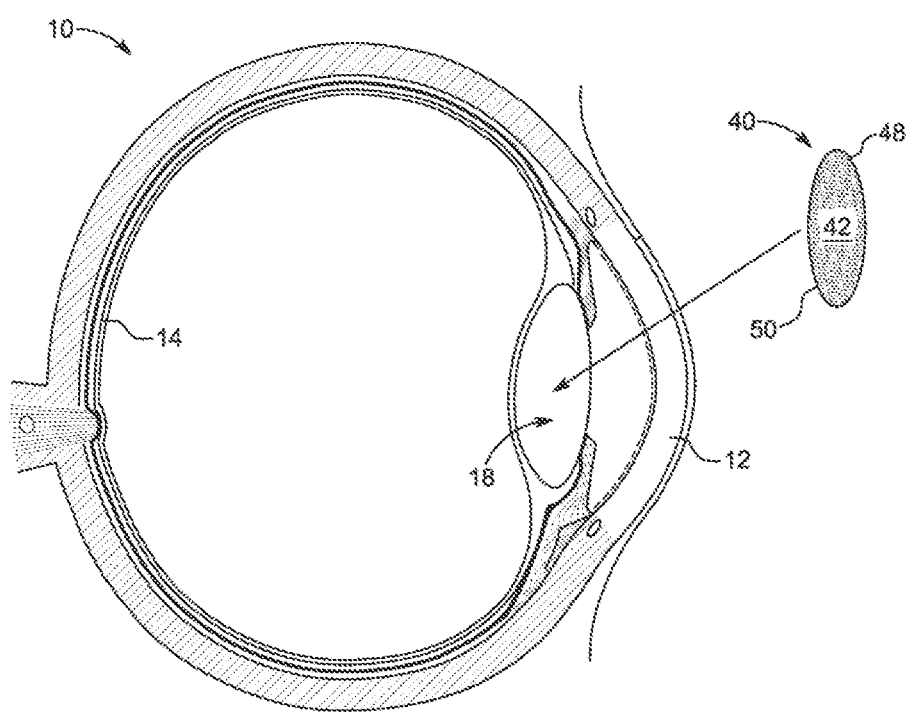
FIG. 2 is a schematic view of an embodiment of an eye with an intraocular implant device in accordance with the present disclosure positioned for installation into the open lens chamber of the eye.

The present disclosure provides a new type of implant device for installation into an empty lens chamber 18, as shown in FIG. 1. For example, as seen in FIG. 2, an intraocular implant device 40 is shown outside of the eye 10 for implantation into empty lens chamber 18 of eye 10. Intraocular implant device 40 includes an anterior side 48 positioned to face cornea 12 after implantation, and a posterior side 50 positioned to face retina 14 after implantation. Intraocular implant device 40 includes numerous technological innovations, and is operable to provide artificial sight improvement or sight restoration.

Intraocular Photoelectric Power Supply (IO-PEPS)

One aspect of intraocular implant device 40 provides an electrical power supply configured to generate electrical power for use by on-board electronics on the intraocular implant device 40 or alternatively housed within the eye. As such, the intraocular implant device 40 includes an intraocular photoelectric power supply (IO-PEPS) device.

Figure 3:
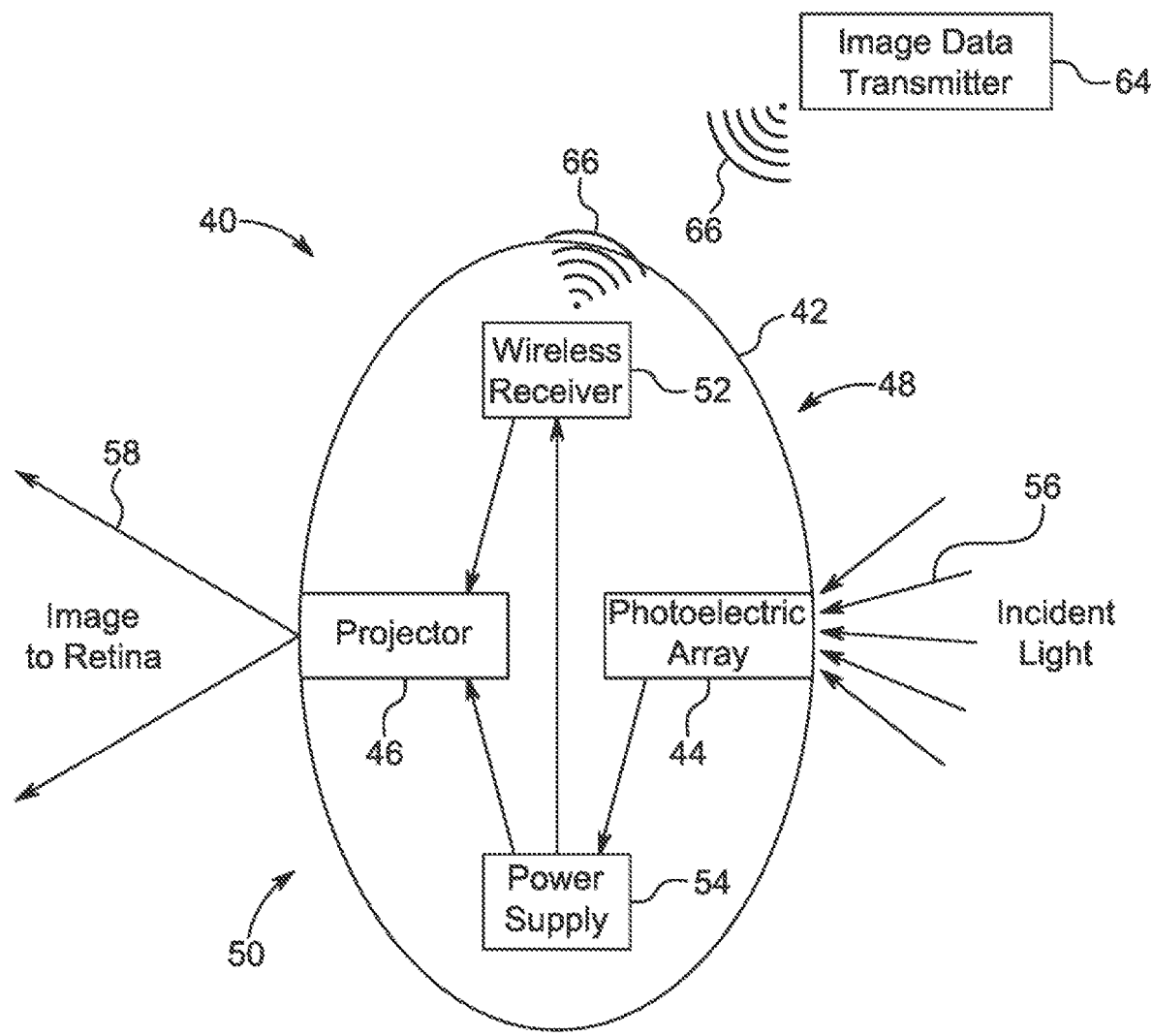
FIG. 3 is a schematic view of an intraocular implant device in accordance with the present disclosure.

As seen in FIG. 3, in some embodiments, intraocular implant device 40 includes a body 42 having an anterior side 48. A photoelectric array 44 including one or more photoelectric sensors is positioned on anterior side 48. Such sensors include any suitable photovoltaic or photoelectric sensors known in the art capable of converting incident light 56 received upon photoelectric array 44 into electricity. Photoelectric array 44 covers a portion of the surface of the anterior side 48 of implant device 40. Photoelectric array 44 includes at least one electrical output operable to transmit electric power to a circuit component. In some embodiments, photoelectric array 44 is coupled to a power supply 54, as shown in FIG. 3. Power supply 54 includes any suitable power converter or power storage device on intraocular implant device 40. Power supply 54 in some embodiments includes a battery configured for storing electrical power generated by photoelectric array 44 for later use by one or more other circuit components. Power supply 54 may be continuously recharging as additional incoming light is incident on photoelectric array 44 and also simultaneously distributing electrical power to other circuit components.

Intraocular implant device 40 is generally opaque when housed within the lens chamber 18 such that incident light 56 entering the eye does not pass optically through the lens body 42. Thus, all incident light entering the eye may be utilized by photoelectric array 44 for energy conversion. As such, the incident light 56 entering the eye may be manipulated to various characteristics for optimization of photoelectric conversion by photoelectric array 44. For example, in some embodiments, various photoelectric cells used in photoelectric array 44 provide improved energy conversion efficiencies when the incident light 56 has a chrominance in a spectral bandwidth tuned specifically to the properties of the photoelectric junctions.

Additionally, because the intraocular implant device 40 is generally opaque in some embodiments, and because the cornea may generally withstand greater luminance than the retina can, the incident light 56 may be further tuned to have increased luminance over natural light to further optimize energy conversion in photoelectric array 44. Thus, the incident light 56 may be generated using an external light source with modulated chrominance and luminance characteristics as compared to natural light to further improve power generation from the intraocular photoelectric power supply.

Your Eye As the Screen (YEATS)

One application of the IO-PEPS feature on an intraocular implant device 40 is to power a projector device 46, shown for example in FIG. 3, housed on the same implant device 40 or otherwise disposed within the eye 10. For example, projector 46 may include any suitable light emitter positioned within the eye in an orientation to project a generated image 58 onto the retina. The emitted light from the projector 46 is incident on the retina much in the way natural light may be incident on the retina after passing through the cornea and the lens. However, in patients with damaged cornea tissue or damaged lens tissue, by the time the light entering the eye makes it to the retina the light pattern is greatly distorted or blocked entirely, causing vision to be distorted or blurred, or causing blindness. By placing a rearward-facing projector 46 on an intraocular implant device 40, an artificial image may be projected onto the retina to simulate natural light, thereby allowing a user to see the artificial image generated by the projector much like the patient would see normally using natural light. A significant difference is that, when using projector 46, the generated image 58 may be controlled to include image data from any source, so the patient's vision may be enhanced or replaced entirely over the field of view available from natural light.

During use, projector 46 is powered by electric power generated on-board the intraocular implant device 40 using photoelectric array 44. Photoelectric array 44 generates enough electric power to operate projector 46 either directly, or through a power supply 54. In some applications, projector 46 may be turned off remotely while allowing photoelectric array 44 to charge power supply 54. Once a sufficient amount of energy is stored in power supply 54, projector 46 may be turned on wirelessly, and photons may be emitted by projector 46 using one or more light emitters. The generated image 58 is then illuminated onto retina 14 through the eye. The retina 14 processes the incident light much like it would natural light, forming an image in the brain and allowing a user to perceive the image.

Figure 4:
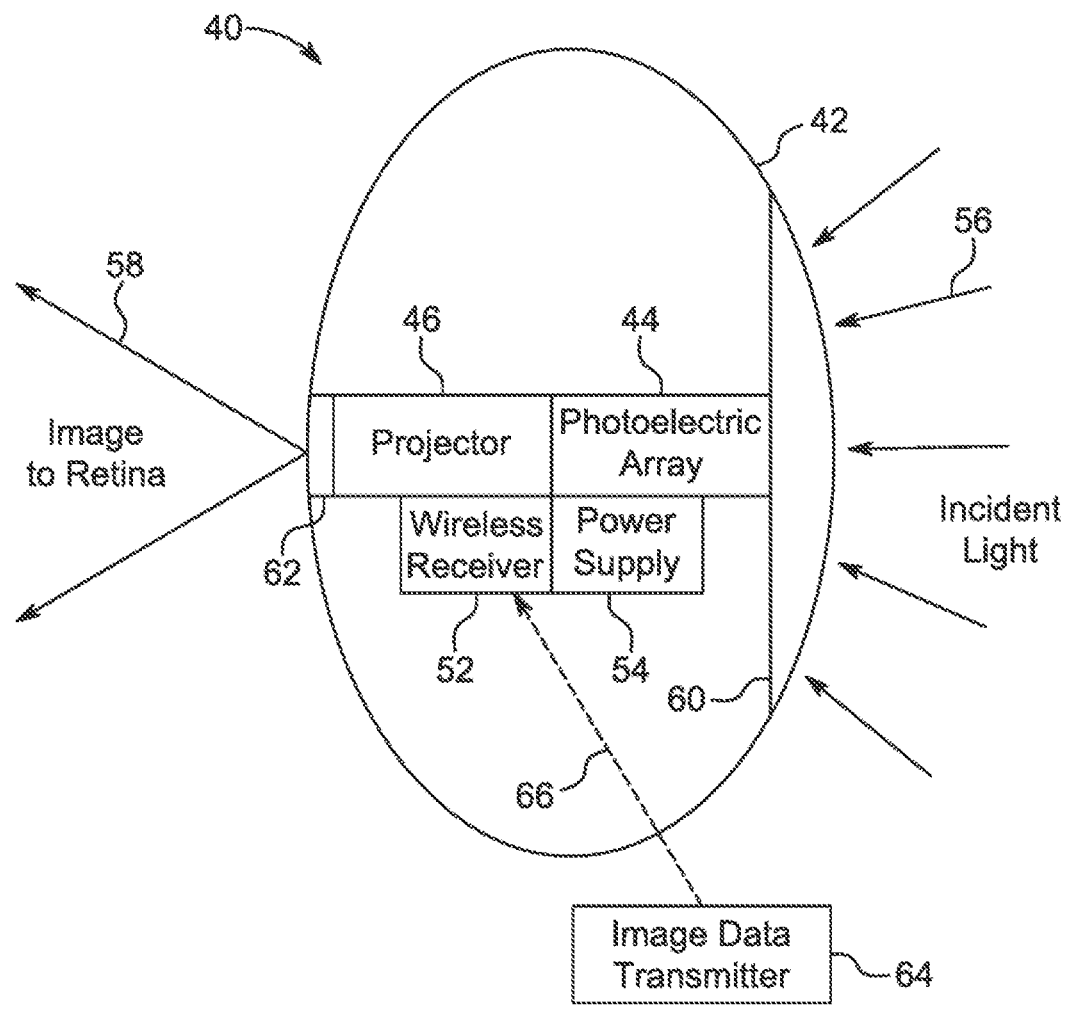
FIG. 4 is a schematic view of an intraocular implant device in accordance with the present disclosure.

The generated pattern of photons or a generated image 58 projected onto the retina 14 is generated by projector 46 using an input signal 66 received by a wireless receiver 52 in some embodiments, as seen in FIG. 3 and in an alternative embodiment in FIG. 4. Input signal 66 includes information associated with the photon pattern to be generated by one or more light emitters within projector 46. Thus, the projector 46 is configured to receive a digital input signal including the image data, and to emit photons from the light projector onto the retina in a pattern representative of the image data. The input signal 66 is passed to intraocular implant device 40 wirelessly from a remote transmitter 64. The input signal 66 is passed to a wireless receiver 52 housed on-board the implant device 40 or alternatively housed at another location within the eye. In some embodiments, wireless receiver 52 is integrated onto projector 46 such that the two are combined as a single unit with wireless data receiver or transmission capabilities. Image data transmitter 64 includes any suitable external device for communicating an input signal 66 to intraocular implant device 40, and specifically to wireless receiver 52 on intraocular implant device 40. Any suitable wireless signal transmission protocol for transmitting data or analog signals associated with imagery may be used for input signal 66.

Once the input signal 66 is received by intraocular implant device 40, the signal is passed to the projector 46, and the projector executes instructions associated with the signal to generate photons representative of an image to be displayed on the retina. In some embodiments, the input signal 66 corresponds to photographs, text, illustrations, videos or any other image data.

As shown in FIG. 3 and FIG. 4, in various embodiments, power supply 54 is also connected to wireless receiver 52 in some embodiments. Thus, power supply 54 may simultaneously supply power to projector 46 and to wireless receiver 52, if necessary. Alternatively, in some embodiments, photoelectric array 44 provides generated electricity directly to wireless receiver and projector.

Wireless receiver 52 may be positioned at any suitable location on intraocular implant device 40, including on a common circuit board structure with one or more other circuit components, such as but not limited to power supply 54, projector 46, photoelectric array 44 or other components. In some embodiments, one or more antennae are connected to wireless receiver 66 to enhance reception of input signal 66 from image data transmitter 64. In some embodiments, the device may be configured to provide enhanced low-light vision or night vision by using an external image data source that acquires an image using a material that responds more quickly than the retina, or by using a material that selectively processes incoming light with higher sensitivity.

One aspect of the present disclosure provides a system that may improve vision over natural analog vision. For example, when natural light enters the eye, the light incident on the retina is limited by the amount of light entering through the cornea and lens. However, using projector 46, additional, higher resolution light patterns may be projected onto the retina to improve or enhance vision over natural analog vision.

Figure 8:
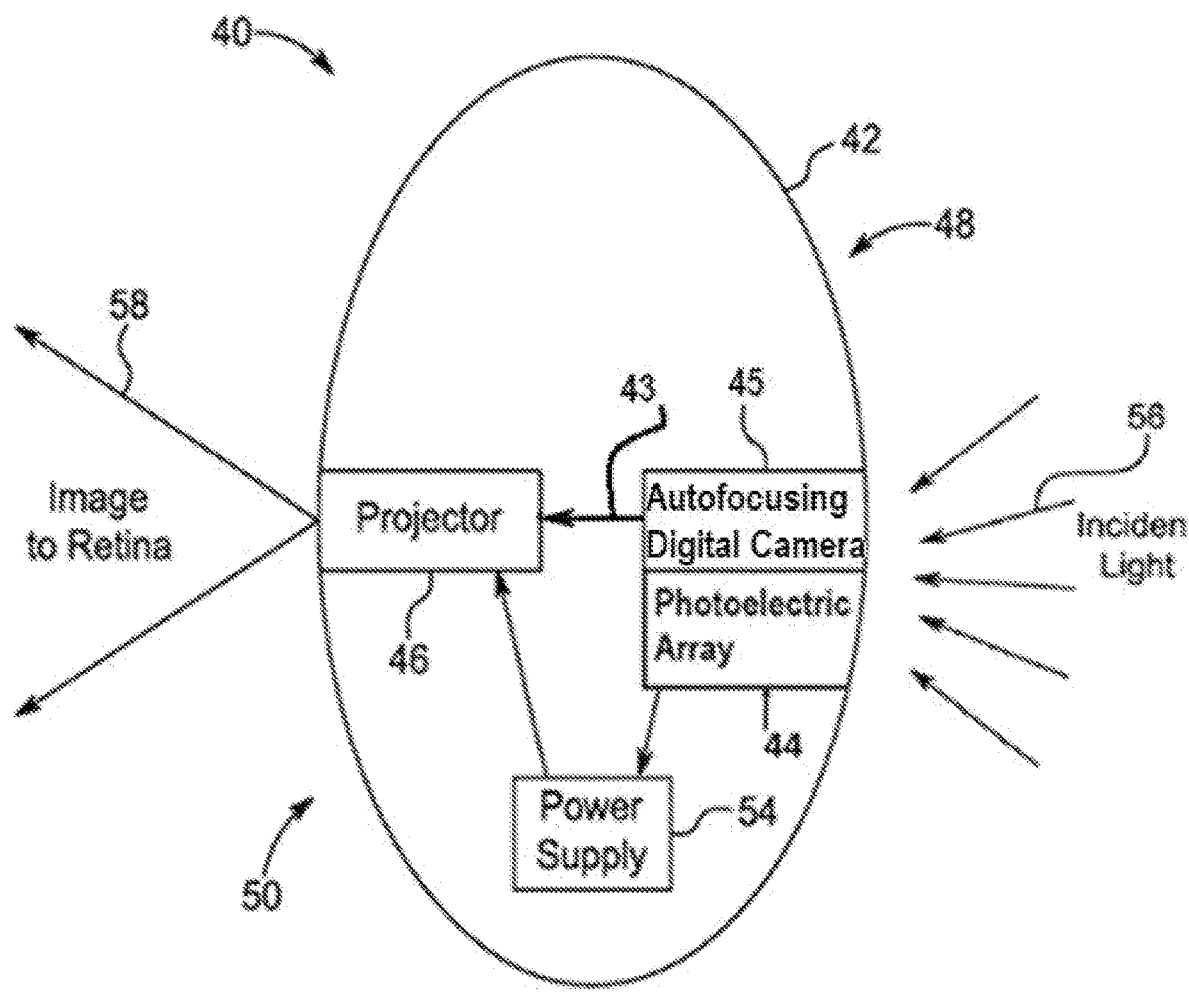
FIG. 8 is a schematic view of an intraocular implant device with an autofocusing digital camera, a photoelectric array, a power supply, and a projector.

As depicted in FIG. 8, in some embodiments, an autofocusing digital camera 45 can be provided with projector 46. The autofocusing digital camera 45 can comprise any digital camera module that is capable of being disposed on the anterior side 48 of the intraocular implant device 40 and is operable to receive incident light 56 through cornea 12, actively adjust internal camera lens(es) to focus the incident light 56, convert the focused incident light into focused image data 43, and send the focused image data 43 to projector 46. For example, in one embodiment, the autofocusing digital camera 45 could comprise an OmniVision OVM6948 CameraCubeChip™—a fully packaged, wafer-level camera module measuring 0.65 mm (W)×0.65 mm (L)×1.158 mm (H) camera module. In other embodiments, digital camera 45 could comprise a NanEyeC camera module made by Austrian company AMS and having a footprint of 1×1 mm, or even the "3D-printed Eagle Eye"—a compound microlens system created by German researchers at the University of Stuttgart and measuring 300×300 μm with a height of <200 μm. In some embodiments, digital camera 45 can utilize any suitable lens to focus the incident light 56, while other embodiments may utilize multiple hard lenses capable of being mechanically adjusted in order to focus the incident light 56. In other embodiments, autofocusing digital camera 45 can additionally feature a digital zoom functionality, making it capable of enlarging portions of the focused image data 43.

In some embodiments, autofocusing digital camera 45 can be powered by photoelectric array 44 and power supply 54. However, in other embodiments, the autofocusing digital camera 45 can be integrated with the photoelectric array 44 such that the two are combined as a single unit. In such embodiments, in addition to gathering light 56 to provide focused image data 43 to projector 46, the autofocusing digital camera 45 is also capable of and responsible for gathering light 56 to power the projector 46 and any other circuit components that may be included.

Figure 9:
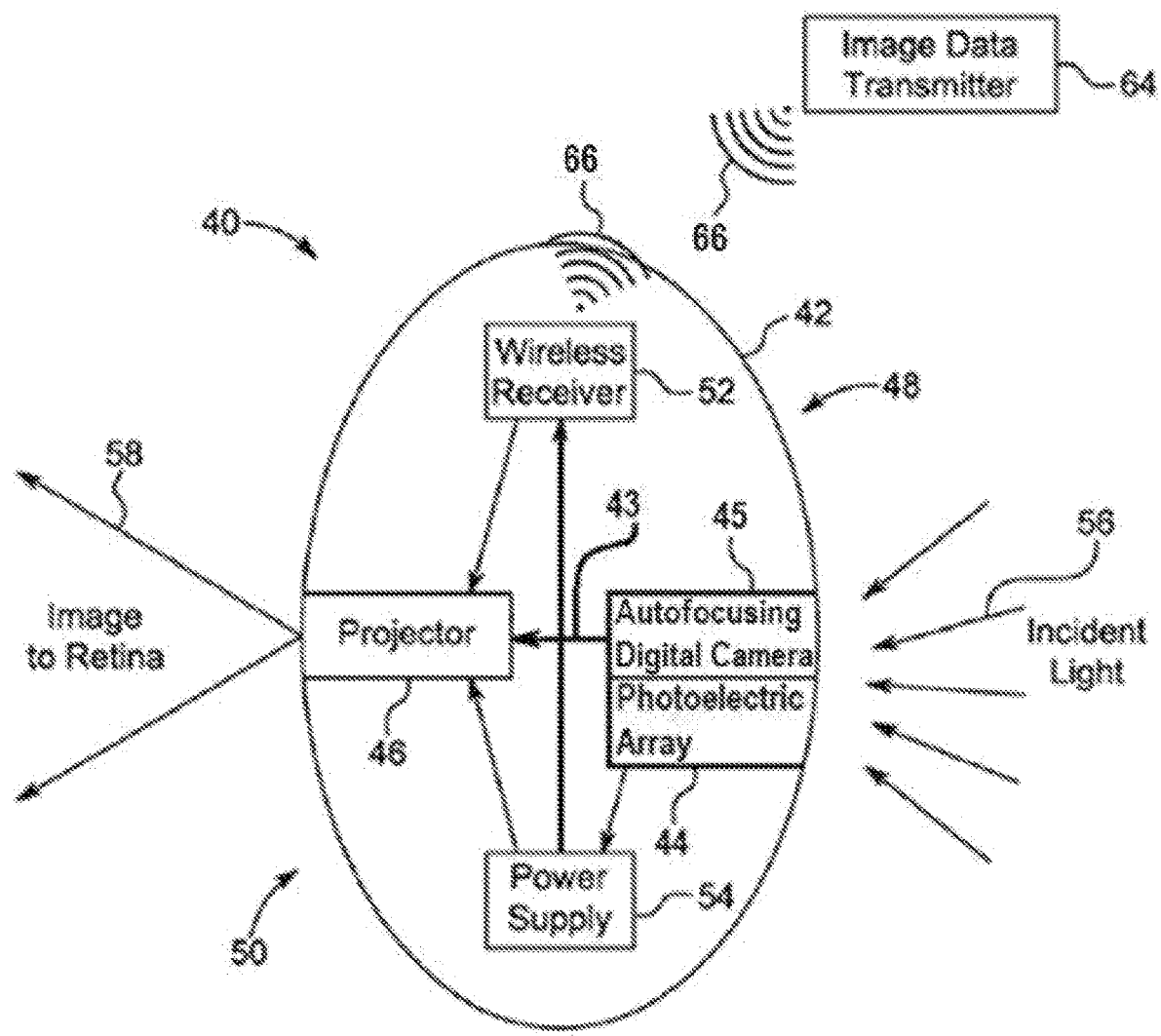
FIG. 9 is a schematic view of an intraocular implant device with an autofocusing digital camera, a photoelectric array, a power supply, an external transmitter, a wireless receiver, and a projector.

In some other embodiments, like that shown in FIG. 9, autofocusing digital camera 45 can be provided in conjunction with both the projector 46 and the wireless receiver 52. In such embodiments, projector 46 may have a multi-channel input capable of receiving one or both of the focused image data 43 and/or the input signal 66. Also in such embodiments, power supply 54 can be simultaneously connected and supply power to the autofocusing digital camera 45, projector 46, and wireless receiver 52. In alternative embodiments wherein the autofocusing digital camera 45 is integrated with the photoelectric array 44, autofocusing digital camera 45 may simultaneously supply power to projector 46 and wireless receiver 52.

Artificial Vision System

Figure 5:
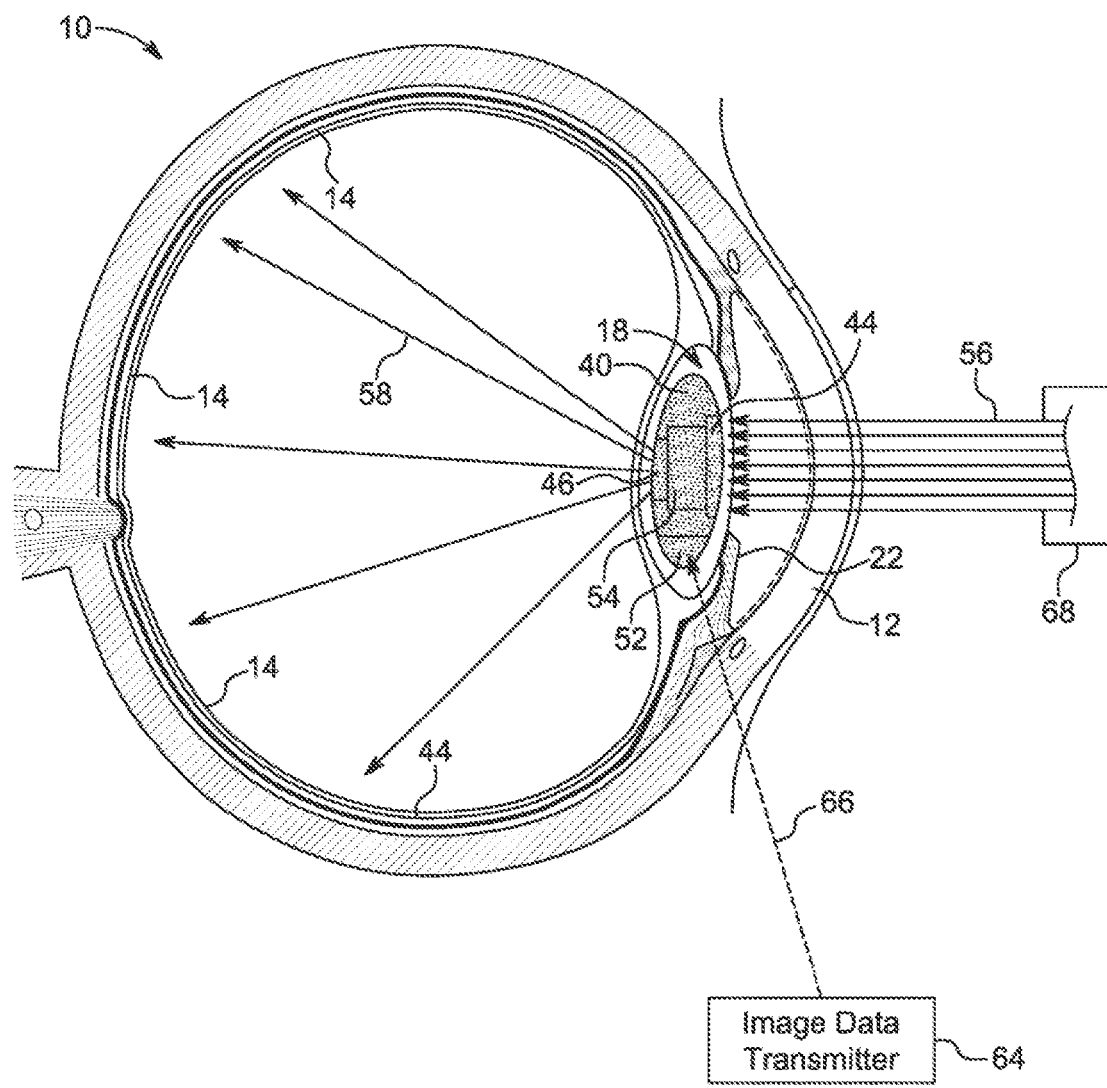
FIG. 5 is a schematic view of an embodiment of an eye with an intraocular implant device in accordance with the present disclosure installed in the lens chamber, and an external light source irradiating the anterior side of the intraocular implant device through the cornea.

Referring now to FIG. 5, an artificial vision system includes an intraocular implant device 40 including an intraocular photoelectric power supply, including a photoelectric array 44 disposed on the anterior side of implant device 40 facing toward the cornea 12. Additionally, a projector 46 is disposed on the posterior side of implant device 40 facing the retina 14. An external light source 68 generates a beam of artificial incident light 56 directed toward the cornea. The generated artificial light 56 is produced solely for the purpose of powering the intraocular photoelectric power supply housed on intraocular implant device 40 installed in the lens chamber 18 within the eye 10. The generated artificial light 56 is tuned in both chrominance (wavelength and frequency) and luminance (brightness) to provide optimized energy conversion and electric power generation inside the photoelectric array 44. The power generated by photoelectric array 44 is used to charge power supply 54, and is subsequently used to power projector 46 to generate a pattern of photos or a generated image 58 for irradiation of the retina 14. Thus, the only light incident on the retina 14 is the light generated by the projector 46.

An external transmitter 64 sends a wireless input signal 66 to intraocular implant device 40. Input signal 66 is received by a wireless receiver 52 on the implant device 40, and the input signal 66 is passed to projector 46 to determine the pattern of generated photons or a generated image 58 projected onto retina 14 by projector 46. Input signal 66 can include data packets corresponding to image data from any source, such as an external camera.

As seen in FIG. 5, the incident light beam 56 generated by external light source 68 is collimated in some embodiments to align with the opening of the iris 22 such that the light will be incident on the photoelectric array 44. In some embodiments, photoelectric array 44 is dimensioned to correspond to the surface region on the body 42 of intraocular implant device 40 aligned with the circular opening defined by the iris 22.

Figure 6:
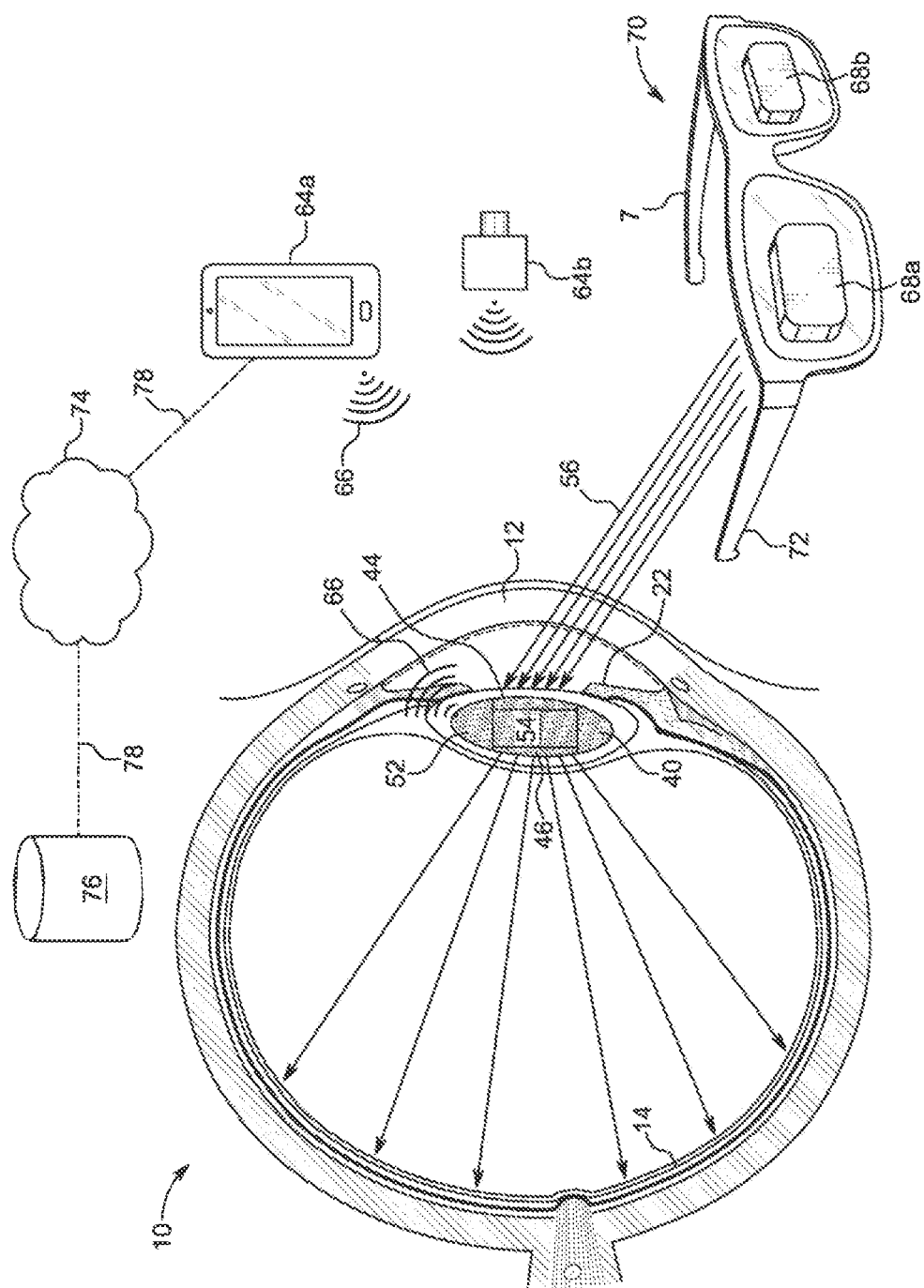
FIG. 6 is a schematic view of an embodiment of an eye with an intraocular implant device in accordance with the present disclosure installed in the lens chamber, and an external light source irradiating the anterior side of the intraocular implant device through the cornea while the intraocular implant device receives a wireless image data signal from a remote transmitter.
Figure 7:
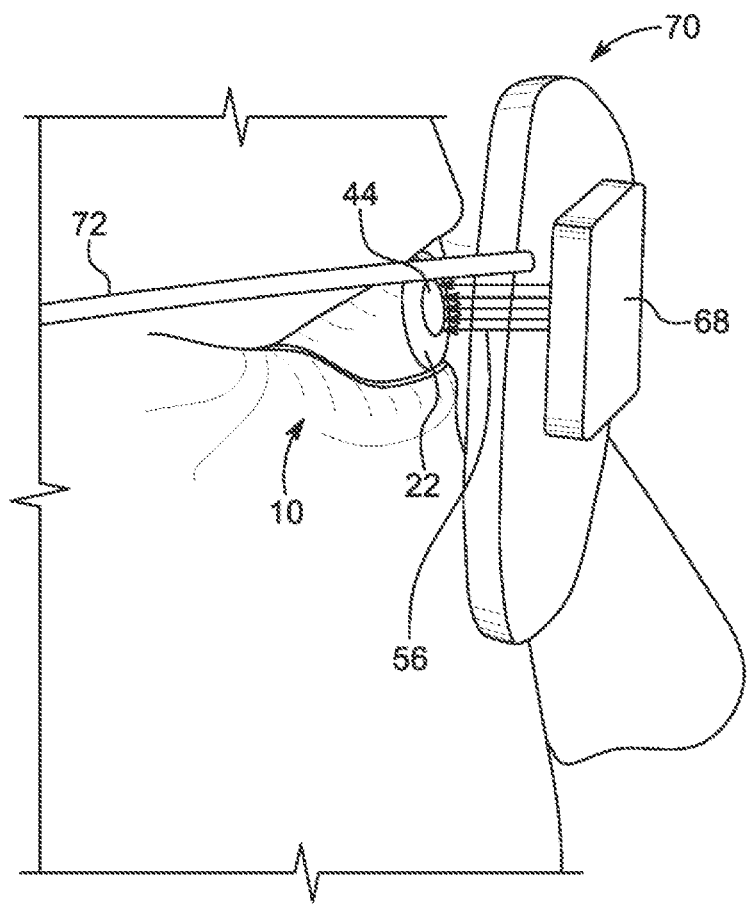
FIG. 7 is a schematic view of an embodiment of an intraocular implant device including an intraocular photoelectric power supply and an external light source irradiating light through the cornea onto the photoelectric array included on the implant installed in the lens chamber in the eye.

Referring to FIG. 6 and FIG. 7, in additional embodiments, external light source 68 may include a wearable technology including one or more light emitters spaced from the eye 10 and configured to emit light back toward the eye 10 for the specific purpose of powering one or more intraocular photoelectric power supply (IO-PEPS) devices housed in the lens chamber 18 in one or both eyes. For example, in some embodiments, a wearable eyeglass frame 70 includes a first external light source 68a and a second external light source 68b. Frame 70 includes first and second temples 72 positioned to engage a user's head, as shown in FIG. 7. Each external light source 68 emits a beam of artificial light back toward the user's eye 10. The beam of generated external light 56 passes into the eye through the cornea 12, and is incident on the photoelectric array 44 on intraocular implant device 40 housed in lens chamber 18. The external light source 68 includes any suitable source of light for powering photoelectric array 44. The light emitted by external light source 68 does not pass directly through the eye to the retina. Instead, the light is converted into electrical energy via the photoelectric array 44, and is then subsequently converted back into photons using projector 46 to project a desired pattern corresponding to an image onto the retina 14.

As shown in FIG. 6, the image generated by projector 46 may come from many different sources. In some embodiments, transmitter 64a includes a mobile device such as a cell phone, laptop, tablet computer, television, or other external electronic device. In some embodiments the transmitter 64a is a video camera which transmits a video feed. Transmitter 64a may include locally stored image data to be used for input signal 66. Alternatively, transmitter 64a may connect dynamically to a remote image storage database 76 via a network, or cloud 74 to access content for input signal 66. In some embodiments, digital image content, such as movies, images, etc. are streamed from a remote database 76 via a network 74 using network signals 78 to provide access to image data for input signal 66.

Referring further to FIG. 6, in some embodiments, an external camera 64b is also configured to produce an input signal 66. The camera 64b is positioned to acquire image data associated with the camera's field of view. The camera 64b may be local to a user, for example may be installed on eyeglass frame 70, or the camera 64b may be remote such that the field of view of the camera is not in the vicinity of the user. The artificial vision system allows a user to dynamically change the input on projector 46 such that the projector 46 may select to display an image pattern associated with input signal 66 from first transmitter 64a or alternatively from camera 64b. In additional embodiments, camera 64b may instead include a second transmitter such as a cell phone, smart phone, laptop, tablet computer, television, or other external electronic device. In some embodiments, projector 46 includes multiple input channels, and is selectively operable to display image data associated with each separate channel, thereby allowing a user to switch between input signals from different external image data sources.

Non-Medical Uses

The above referenced devices may also be utilized for non-medical applications such as consumer entertainment, professional vision augmentation, virtual reality content generation and display, military applications, or other non-medical applications. For example, in some embodiments, a user with an intraocular implant device 40 installed in one eye is able to selectively turn on the device to receive image data from any external source via input signal 66. The user may be able to maintain a natural lens in the second eye to continue to rely on natural analog vision when not using device 40. As such, the intraocular implant device 40 provides an implantable brain-machine interface capable of delivering digital image content to the user through an image projected directly onto the retina 14. The image may be manipulated in many ways prior to projection by projector 46 that are not possible via standard analog light transmission through the cornea and lens. This makes enhanced, augmented and artificial vision possible. In some embodiments, this embodiment may be referred to as MAGITAL.

Medical Uses

The above-referenced devices and methods may also be used in medical applications for sight restoration or sight improvement. In such medical applications a patient may receive an intraocular implant device 40 in the lens chamber of each eye. The patient may then utilize a wireless transmitter 64 to transmit image data from an external source to each intraocular implant device 40. The transmitter 64 includes a camera oriented toward the user's local environment in some applications simulating natural vision. Alternatively, transmitter 64 includes an auxiliary input from some other source of digital image content, such as computer, mobile phone, tablet or other source. Medical patients with conditions such as cornea damage may primarily rely on the intraocular implant devices 40 to provide artificial vision where natural analog vision simply is no longer possible due to the inability of light to properly enter and pass through the eye to the retina.

The present disclosure further provides associated methods of modifying, improving, restoring, augmenting or restoring vision in humans and animals using the previously-described devices and techniques. For example, a method of restoring vision in an eye comprises the steps of: (1) providing an intraocular implant device including an anterior side and a posterior side, a photoelectric array on the anterior side, and a projector on the posterior side; (2) positioning the intraocular implant device in the lens chamber of the eye such that the photoelectric array faces the cornea and the projector faces the retina; (3) illuminating the photoelectric array with input light from an external light source; (4) converting the input light into electrical energy via the photoelectric array; (5) powering the projector using the electrical energy converted by the photoelectric array; and (6) projecting photons generated by the projector onto the retina, wherein the projected photons correspond to digital image data received wirelessly by the intraocular implant device from a remote transmitter. The method may further comprise sending a wireless input signal to the projector from an external transmitter, wherein the wireless input signal contains image data; emitting photons from the projector in a pattern representative of the image data; providing an external light source positioned to emit light towards the photoelectric sensor; receiving the light in the photoelectric sensor; converting the light into electrical energy; and powering the intraocular implant device with the electrical energy.

Refraction Adjustment Unit

Figure 10:
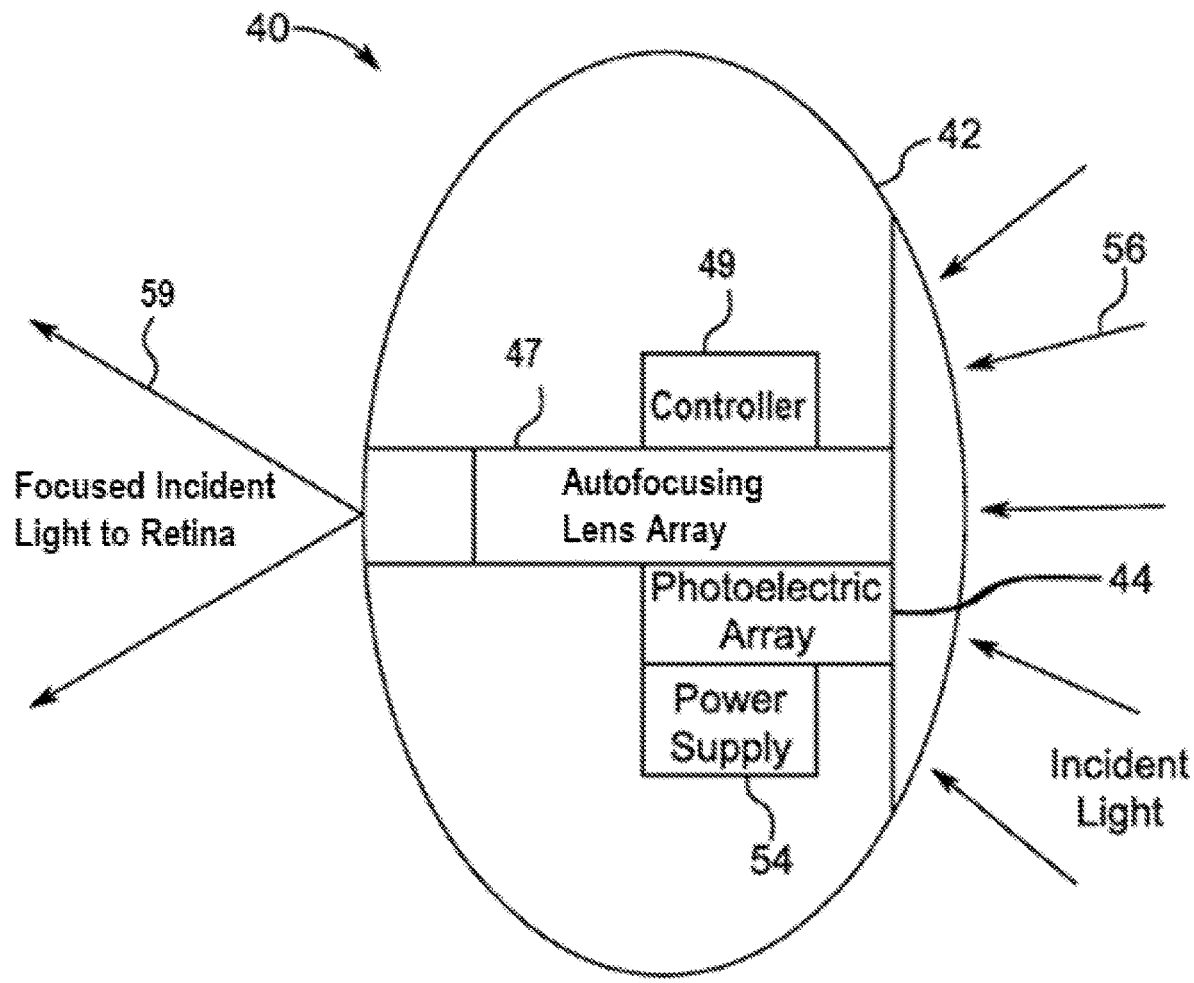
FIG. 10 a schematic view of an intraocular implant device with an autofocusing electromechanical lens array, a controller, a photoelectric array, and a power supply.

The embodiment depicted in FIG. 10 is known as a Refraction Adjustment Unit and shows another application of the IO-PEPS feature on an intraocular implant device 40, wherein the IO-PEPS is being used to power an autofocusing electromechanical lens array 47 and a controller 49 housed on the same intraocular implant device 40 or otherwise disposed within the eye. In a Refraction Adjustment Unit, the autofocusing electromechanical lens array 47 may include any suitable lens array positioned within the lens implant 40 to receive incident light 56 through the anterior side 48 of the lens implant 40, actively adjust the incident light 56 as it passes through the lens array 47 until the light 56 becomes focused, and transmit the focused incident light 59 to the retina 14. In some embodiments, a controller 49 is also provided and may include any suitable controller positioned within the lens implant 40 to be in communication with the autofocusing electromechanical lens array 47, analyze the incident light 56 passing through the lens array 47, and actively adjust the lens array 47 until the light 56 is focused. In other embodiments, the controller 49 can be integrated with the autofocusing electromechanical lens array 47 such that the two are combined as a single unit. When implanted in a user's lens chamber 18, the Refraction Adjustment Unit depicted in FIG. 10 can essentially operate as a multifocal lens embedded in the user's eye and can eliminate the user's need for reading glasses or bifocals.

In some embodiments, the Refraction Adjustment unit embodied in FIG. 10 is only capable of operating in an "optical mode," wherein no digital signal is involved and nothing but focused incident light 59 actively passes through the lens 40 to the retina 14. However, in another embodiment being shown in both FIG. 11 and FIG. 12, the Refraction Adjustment Unit can be optionally operated in either an "optical mode" or a "digital mode." In this embodiment, the autofocusing electromechanical lens array 47 can be used in conjunction with a wireless receiver 52, an external transmitter 64, and a projector 46, wherein the projector 46 is capable of being mechanically situated in an engaged position or an unengaged position. When the Refraction Adjustment Unit is operating in an "optical mode," as in FIG. 11, the projector 46 is mechanically situated in an unengaged position and inactive, while the autofocusing electromechanical lens array 47 is active and transmitting focused incident light 59 to the retina 14. The Refraction Adjustment Unit in "optical mode," in FIG. 11, operates in the same matter as the embodiment of the Refraction Adjustment Unit depicted in FIG. 10.

When operating in optical mode, the device may include autonomous functions to use ghost signals associated with natural tissue, such as electrical signals sent to nerves or muscles present in or around the eye. Such signals may be associated with electrical activity, used to control motion or associated with a pressure change.

Figure 11:
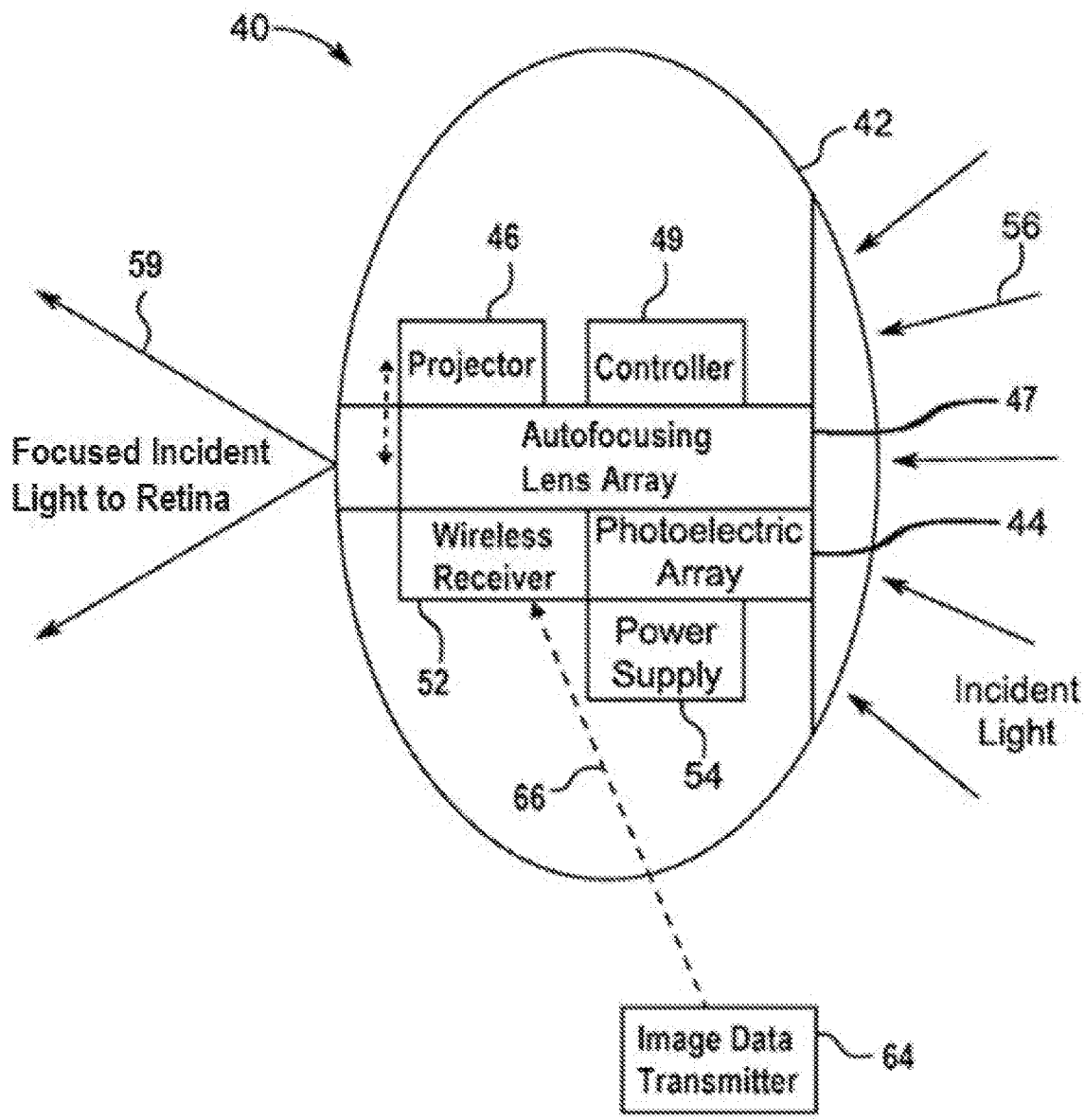
FIG. 11 is a schematic view of an intraocular implant device with an autofocusing electromechanical lens array, a controller, a photoelectric array, a power supply, an external data transmitter, a wireless receiver, and a projector mechanically situated in an unengaged position.
Figure 12:
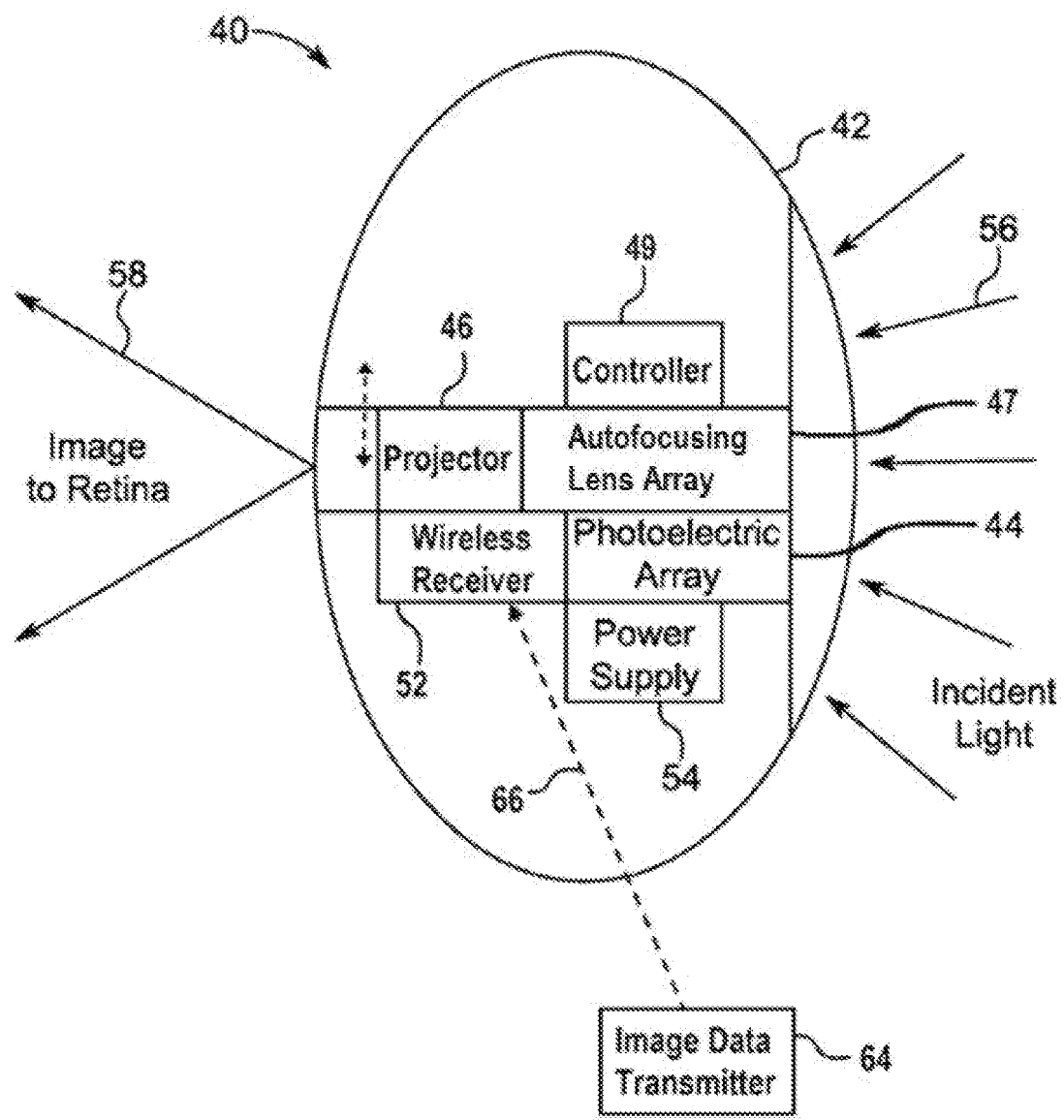
FIG. 12 is a schematic view of the intraocular implant device of FIG. 7, wherein the projector is now mechanically situated in an engaged position.

On the other hand, when the Refraction Adjustment Unit is operating in a "digital mode," as depicted in FIG. 12, the projector 46 is mechanically situated in an engaged position and active, while the autofocusing electromechanical lens array 47 is now inactive. While operating in a "digital mode," an external transmitter 64 is operable to wirelessly send a digital input signal 66 including image data, a wireless receiver 52 disposed on the intraocular implant body 40 is operable to wirelessly receive the digital input signal 66 and to transmit the digital input signal to the projector 46 mechanically situated in the engaged position, and the projector 46 is disposed on the posterior side 50 of the intraocular implant body 40 and is operable to receive the digital input signal 66 including image data, and to emit photons from the projector onto the retina 14 in a pattern representative of the image data 58. Thus, in such an embodiment of the Refraction Adjustment Unit, the projector 46 can be selectively engaged to transmit image data 58 to the retina, as in FIG. 12, or unengaged such that natural light can pass through the eye to the retina 14, as seen in FIG. 11.

Figure 13:
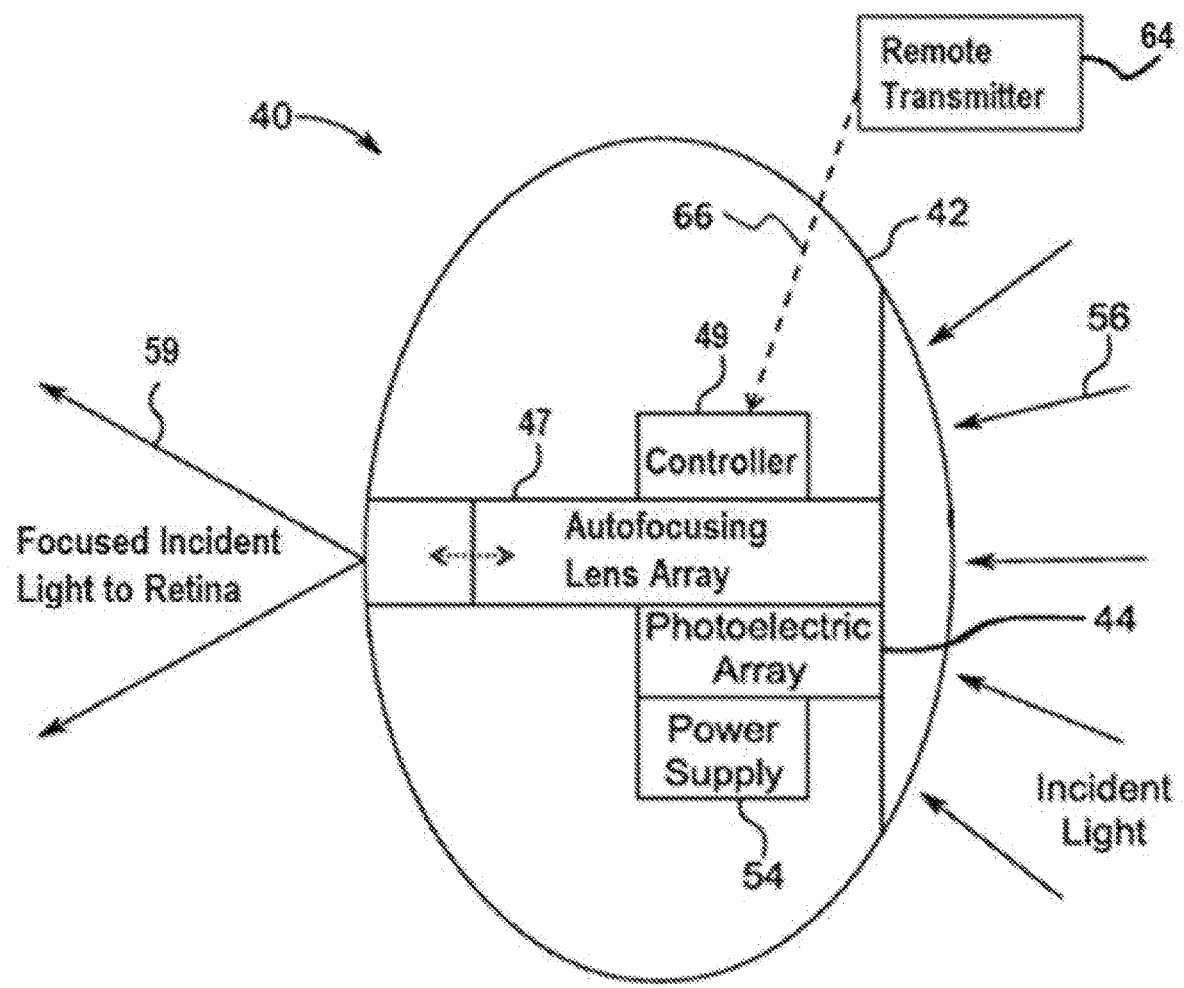
FIG. 13 is a schematic view of an intraocular implant device with an autofocusing electromechanical lens array capable of axial movement, a controller, a photoelectric array, a power supply, and an external data transmitter.

Yet another embodiment of the Refraction Adjustment Unit, shown in FIG. 13, is capable of correcting the vision problems associated with age-related myopia, presbyopia and hyperopia. Age-related myopia, presbyopia and hyperopia are vision conditions attributable to the size of a person's eye, and more specifically to the distance between a person's ocular lens and retina. Myopia, or nearsightedness, occurs when the distance between a person's ocular lens and retina is too large and the incoming light gets focused in front of the retina, whereas hyperopia, presbyopia or farsightedness, occurs when the distance between a person's lens and retina is too small and the incoming light gets focused behind the retina or the lens loses flexibility and makes it difficult to focus on near-field objects. As humans get older, the age-related effects of myopia, presbyopia and hyperopia may get worse as natural distancing between the lens and retina occurs. While the autofocusing electromechanical lens array 47 provides real-time focusing by focusing the incident light 56 and transmitting the focused incident light 59 to the retina, this will not work to address age-related myopia or hyperopia without moving the lens array 47 a few millimeters axially forwards or backwards inside the eye. Thus, in the embodiment illustrated in FIG. 13, the Refraction Adjustment Unit may additionally include a remote transmitter 64 whereby a user can wirelessly send a digital input signal 66 including axial location adjustment data. In this embodiment, the controller 49 is further operable to wirelessly receive the digital input signal 66 and to adjust the axial location of the optical autofocusing lens array 47 between the anterior side and posterior side of the intraocular implant body 40 in accordance with the location adjustment data. Such axial location adjustments can ensure that the outgoing focused incident light 59 is being focused directly on the retina so that the user does not experience the symptoms associated with age-related myopia or hyperopia.

Glucose and Intraocular Pressure Sensors and Pumps

Figure 14:
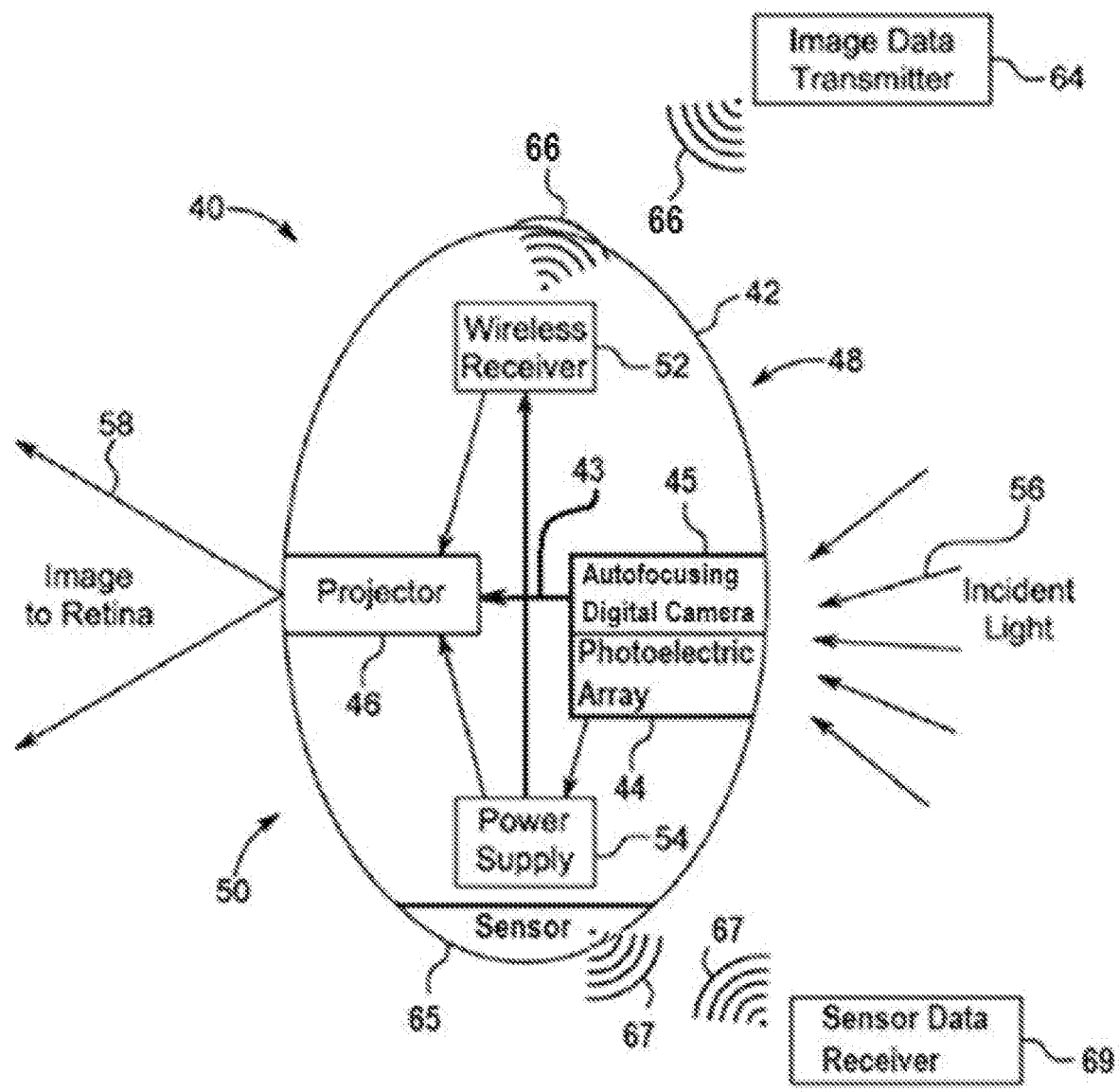
FIG. 14 is a schematic view of an intraocular implant device with an autofocusing digital camera, a photoelectric array, a power supply, an external transmitter, a wireless receiver, a glucose sensor, an external receiver, and a projector.
Figure 15:
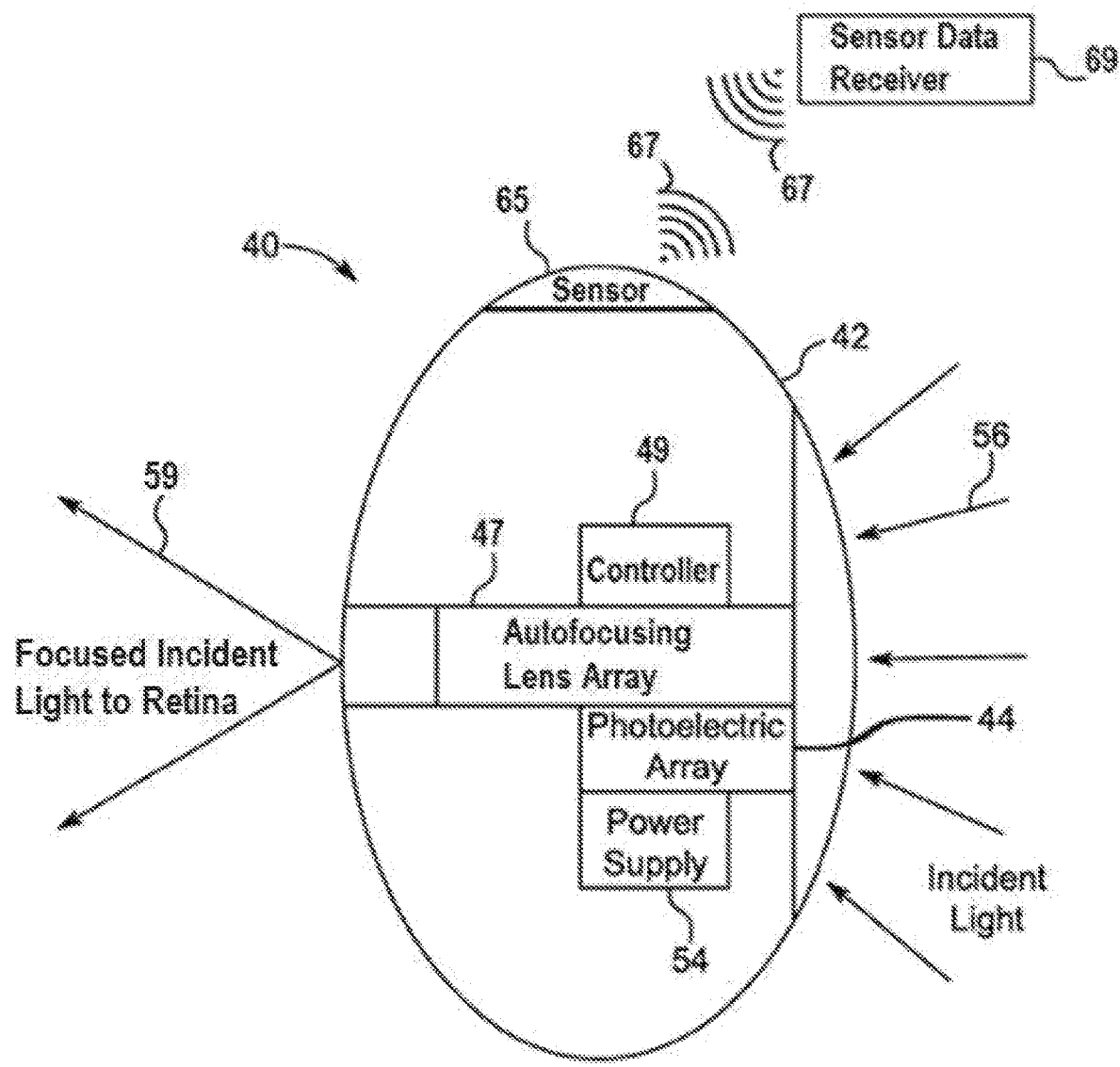
FIG. 15 is a schematic view of an intraocular implant device with an autofocusing electromechanical lens array, a controller, a photoelectric array, a power supply, a intraocular pressure sensor, and an external receiver.

In other embodiments, as in FIGS. 14 & 15, a glucose sensor 65 may be provided as a convenient tool for users to keep track of their blood sugar levels. Such a feature can be of particularly help to diabetic users, who must constantly keep track of their blood sugar levels in order to adjust their insulin intake dosage. In these embodiments, glucose sensor 65 is disposed on an outer portion of the intraocular implant body 40 so that it can physically contact the user's intraocular eye fluids when the intraocular implant body is positioned inside the lens chamber 18 of the user's eye. The glucose sensor 65 is operable to measure glucose in intraocular eye fluids and wirelessly send a digital output signal 67 including glucose measurement data. Also provided in this embodiment is an external receiver 69 operable to wirelessly receive the digital output signal 67, process the digital output signal 67, and store the glucose measurement data included therein.

In some other embodiments, as in FIGS. 14 & 15, an intraocular pressure sensor 65 may be provided as a convenient tool for users to monitor their eye pressure and address any eye pressure abnormalities detected. Normal intraocular pressure generally ranges from 10-21 mmHg and is a signal of generally healthy eye. However, an intraocular pressure greater than 21 mmHg is considered intraocular hypertension, or high eye pressure, and should be addressed by a medical professional immediately as it can either cause or signal to a variety of serious eye conditions such as glaucoma, optic nerve damage, and progressive vision loss. In these embodiments, intraocular pressure sensor 65 is disposed on an outer portion of the intraocular implant body 40, so that it physically contacts a portion of the eye when the intraocular implant body 40 is positioned inside the lens chamber 18 of an eye. The intraocular pressure sensor 65 is operable to measure intraocular eye pressure and wirelessly send a digital output signal 67 including intraocular pressure data. Also provided in this embodiment is an external receiver 69 operable to wirelessly receive the digital output signal 67, process the digital output signal 67, and store the intraocular pressure data included therein.

Both the glucose sensor and intraocular pressure sensor 65 have the capacity and functionality to be integrated into each and every one of the intraocular lens implant embodiments disclosed herein. In further embodiments, a glaucoma pump may be integrated into the device and powered using the on-board electronics and power supply.

In further embodiments, the present disclosure provides comprehensive intraocular vision advancement (CIVA) devices and methods including an adjustable base accommodating lens (ABAL). As an example, an intraocular implant lens replacement may have a desired diopter to correct a patient's far-vision, but such a solution does not address issues associated with accommodation or accommodative dysfunction, especially for reading at close ranges. By providing an adjustable base accommodating lens (ABAL) as part of the intraocular implant, precise base adjustments may be made post-operatively to fine-tune vision. In some embodiments, an adjustable base accommodating lens may be adjusted wirelessly using an input control signal from a peripheral device with a transmitter such as mobile electronic device. By adjusting the base setting following implantation, a user may address myopia or hyperopia by changing the base setting of the lens implant. In some applications, an adjustable base accommodating lens may be utilized to improve vision following lens replacement during cataract surgery.

In further applications, corrective LASIK surgery may be performed prematurely, causing reduction in vision as a patient continues to age. In such situations, an adjustable base accommodating lens may be implanted to correct myopia or hyperopia using the desired lens diopter. As the patient continues to age, accommodation may be provided at the appropriate time by adjusting the settings on the adjustable base accommodating lens to address age-related accommodative dysfunction.

The adjustable base accommodating lens (ABAL) includes one or more optical elements disposed in an intraocular implant that operate to optically correct or enhance light passing through the eye toward the retina to achieve an adjustable base configuration. As a user ages or develops vision-related changes in eyesight, such as but not limited to myopia, hyperopia and presbyopia, the adjustable base accommodating lens can be selectively configured to provide different base and/or accommodation settings to provide far-vision correction and accommodation. In some embodiments, the adjustable base accommodating lens includes a plurality of lenses within the intraocular implant that can be mechanically adjusted in relation to each other and in relation to the eye to achieve adjustable base accommodation. In further embodiments, adjustable base accommodating lens (ABAL) embodiments may employ a variable refractive index lens within the intraocular implant that may be adjusted using mechanical or electromechanical input from a user or physician. The variable refractive index lens includes any suitable variable refractive lens material, including but not limited to an adjustable refractive index material such as but not limited to a polymer, liquid or glass material, or a fixed thin lens with multiple refractive indices to provide a continuum across the lens. One or more lenses in the implant employs variable refractive index technology.

In some embodiments, an adjustable base lens includes a power supply such as a battery to provide power for limited adjustments to the optical elements within the implant without the need for a photoelectric array. In such embodiments, the adjustable base lens may be adjusted using the on-board power supply. Applications for such a device may include situations where adjustment may only be needed a few times for the life of the battery, typically shortly after implantation, and there will be no further need to adjust the optical elements. In such applications, it is not necessary to include a photoelectric array for continuous recharging of the device.

In further embodiments, the lens implant is configured to selectively filter light passing through the optical elements of the implant to provide darkening of the vision field, similar to the properties of sunglasses. In some embodiments, the optical lens assembly within the implant includes one or more shaded lenses that may be deployed optomechanically. Alternatively, in digital embodiments, the shading function can be achieved using a software-based control. In further embodiments, one or more lenses in the optical lens assembly includes photo-chromatic properties to filter light. Any other suitable light filtering modality may be employed to achieve a light filtering feature. Additionally, one or more lenses in the optical lens assembly includes a UV-protective coating to protect the user's retina from undesirable bandwidths of ultraviolet light.

Figure 16:
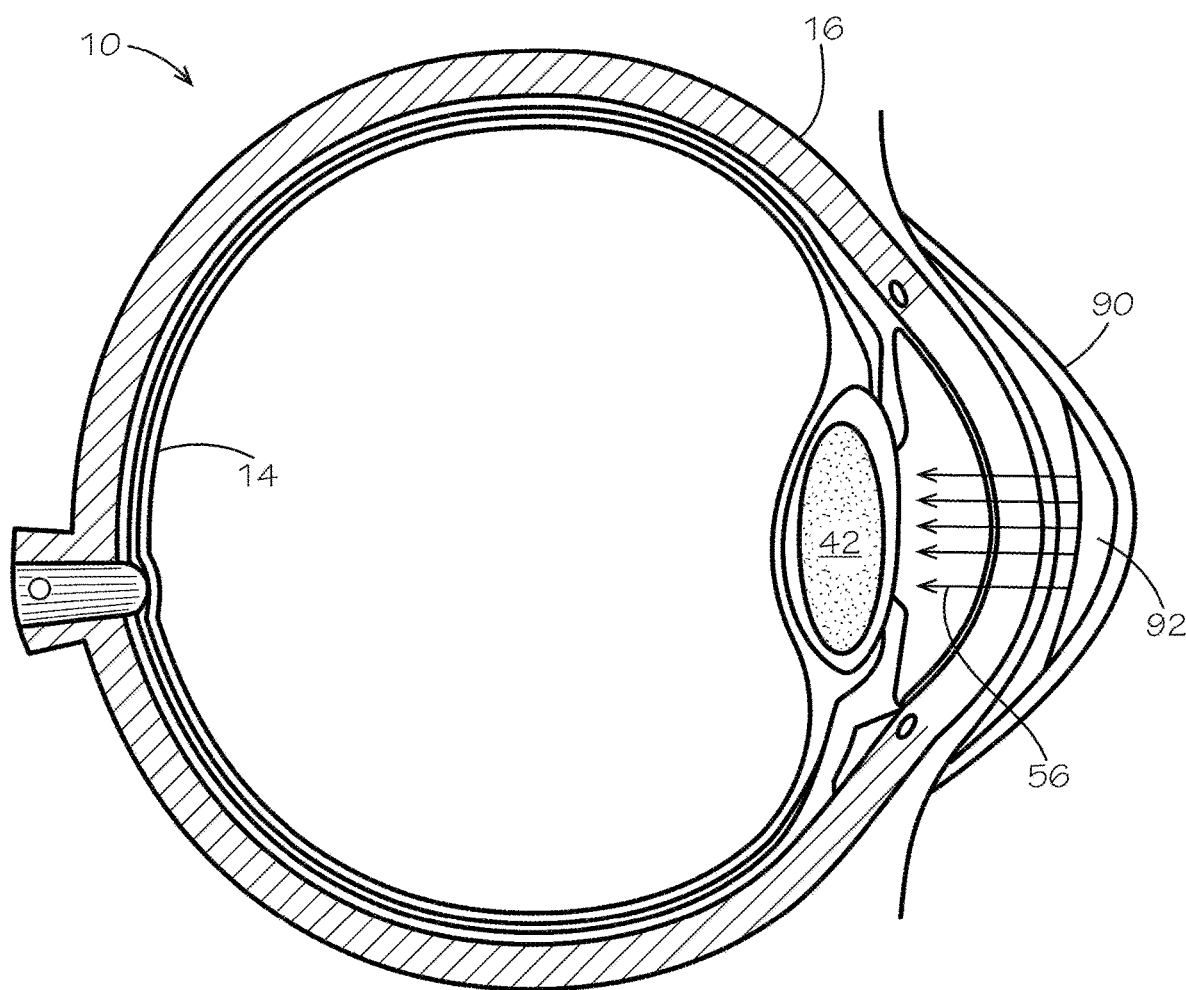
FIG. 16 is a schematic view of an eye including an intraocular implant device and a scleral lens positioned to recharge the implant.

Referring further to FIG. 16, in some embodiments the external light source 68 may be positioned on a scleral contact lens 90 positioned on the exterior of the cornea. The scleral contact lens 90 defines an interstitial space between the scleral contact lens and the retina. In some embodiments, a light emitter 92 is disposed between the scleral contact lens 90 and the retina. The emitter 92 is configured to emit incident light 56 toward the intraocular implant body 42 such that the light may be used by a photoelectric array on the implant to power or recharge the intraocular implant. One advantage of this embodiment is that a user may power or re-charge the intraocular implant when the eye is closed, such as when a user is asleep.

Thus, although there have been described particular embodiments of the present invention of a new and useful COMPREHENSIVE INTRAOCULAR VISION ADVANCEMENT (CIVA), it is not intended that such references to particular embodiments be construed as limitations upon the scope of this invention.

What is claimed is:

1. An intraocular implant device, comprising:
  an intraocular implant body shaped for positioning inside a lens chamber of an eye, the intraocular implant body having an anterior side for facing a cornea of the eye, and a posterior side for facing a retina of the eye;
  an autofocusing electromechanical lens array disposed on the intraocular implant body and operable to receive natural light through the cornea, adjust the natural light received by the lens array, and transmit the adjusted natural light to the retina;
  a controller in communication with the lens array and operable to analyze the natural light received by the lens array and actively adjust the lens array until the natural light adjusted by the lens array is focused;
  a power supply disposed on the intraocular implant body and operable to provide power to one or more components disposed on the intraocular implant body;
  a wireless receiver disposed on the intraocular implant body and operable to wirelessly receive a digital input signal;
  an external transmitter operable to wirelessly send the digital input signal to the wireless receiver;
  a photoelectric sensor operable to receive light through the cornea and to convert the light received by the photoelectric sensor into electrical energy for use with one or more circuit components disposed on the intraocular implant body; and wherein the photoelectric sensor includes a picture element operable to detect chrominance and luminance of the light received by the photoelectric sensor and a photoelectric element disposed proximate the picture element.

2. The device of claim 1, wherein the photoelectric sensor includes a plurality of stacked photoelectric p-n junctions, wherein each stacked photoelectric p-n junction is receptive to a specific bandwidth of light frequencies.

3. The apparatus of claim 1, further comprising a light projector, wherein the light projector is operable to emit photons onto the retina.

4. The device of claim 3, wherein the photoelectric sensor is further operable to convert light received by the photoelectric sensor into image data and to transmit the image data to the light projector.

5. The device of claim 4, further comprising:
a scleral contact lens; and
an exterior light source disposed on the scleral contact lens,
wherein the exterior light source is configured to generate and emit light through the cornea.

6. The device of claim 1, wherein the lens array includes an adjustable base accommodating lens.

7. The device of claim 1, wherein the lens array includes a variable refractive index lens.

* * * * *